(12) United States Patent
Saikali et al.

(10) Patent No.: US 6,716,981 B2
(45) Date of Patent: Apr. 6, 2004

(54) PROCESS FOR THE PREPARATION OF N-(AMINO-4, 6-DIHALO-PYRIMIDINE) FORMAMIDES

(75) Inventors: Elie Saikali, Visp (CH); Walter Brieden, Brig-Glis (CH)

(73) Assignee: Lonza AG, Basel (CH)

( * ) Notice: Subject to any disclaimer, the term of this patent is extended or adjusted under 35 U.S.C. 154(b) by 0 days.

(21) Appl. No.: 09/867,552

(22) Filed: May 31, 2001

(65) Prior Publication Data

US 2001/0031868 A1 Oct. 18, 2001

Related U.S. Application Data

(62) Division of application No. 09/461,244, filed on Dec. 16, 1999, now Pat. No. 6,271,376.
(60) Provisional application No. 60/146,106, filed on Jul. 29, 1999.

(30) Foreign Application Priority Data

Dec. 21, 1998 (EP) ............................................. 98124188
Jan. 18, 1999 (EP) ............................................. 99100788
Apr. 12, 1999 (EP) ............................................. 99107161

(51) Int. Cl.7 ...................... C07D 239/42; C07D 239/30
(52) U.S. Cl. ........................................ 544/320; 546/330
(58) Field of Search ................................. 544/320, 330

(56) References Cited

U.S. PATENT DOCUMENTS 4,929,729 A * 5/1990 Haga et al. ................. 544/330
4,965,270 A   10/1990 Harndon et al. ............ 544/276
5,216,161 A * 6/1993 Hanson et al. .............. 544/330
6,448,403 B1 * 9/2002 Daluge et al. .............. 544/323

FOREIGN PATENT DOCUMENTS

EP          0684236     4/1995
WO       WO 9101310     2/1991

* cited by examiner

Primary Examiner—Richard L. Raymond
Assistant Examiner—Venkataraman Balasubramanian
(74) Attorney, Agent, or Firm—Fisher, Christen & Sabol

(57) ABSTRACT

A process for the preparation of a 2,5-diamino-4,6-dihalopyrimidine of the formula:

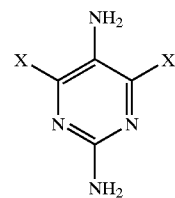

III in which X is a halogen atom, comprising reacting 2,5-diamino-4,6-dihydroxypyrimidine or its salt of the formula:

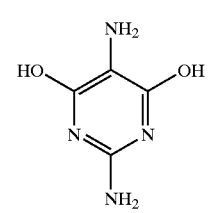

IV with a phosphorus oxyhalide and a quaternary ammonium halide or an amine in a halogenated hydrocarbon as a solvent.

11 Claims, No Drawings

PROCESS FOR THE PREPARATION OF N-(AMINO-4, 6-DIHALO-PYRIMIDINE) FORMAMIDES

This application is a division of U.S. application Ser. No. 09/461,244, filed on Dec. 16, 1999, now U.S. Pat. No. 6,271,376, issued on Aug. 7, 2001, which has priority benefit of U.S. Provisional Application No. 60/146,106, filed on Jul. 29, 1999, which has benefit of European Patent Application numbers: 98124138.8, filed on Dec. 21, 1998; 99100788.1, filed on Jan. 18, 1999; and 99107161.4, filed on Apr. 12, 1999.

DESCRIPTION

The invention relates to a novel process for the preparation of N-(amino-4,6-dihalopyrimidine)-formamides of the formula

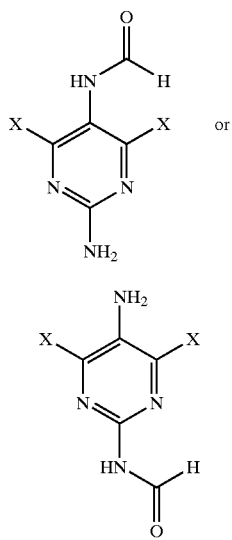

starting from a 2,5-diamino-4,6-dihalopyrimidene of the general formula

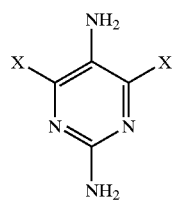

N-(Amino-4,6-dihalopyrimidene)formamides. Such as N-(2-amino-4,6-dihalopyrimidin-5-yl)formamide are important intermediates for the production of antiviral nucleotide derivatives (EP-0 684 236).

To date, a number of processes for the preparation of N-(2-amino-4,6-dihalopyrimidin-5-yl)formamide have been disclosed. Thus EP-A 0 684 236, for example, describes a process for the preparation of N-(2-amino-4,6-dihalopyrimidin-5-yl) formamide starting from an aminomalonic ester. In this process, the aminomalonic ester is first cyclized to 2,5-diamino-4,6-dihydroxypyrimidine with guanidine in the presence of an alkoxide and then 4,6-dichloro-N'-(dimethylaminomethylene) pyrimidene-2,5-diamine is formed from this with phosophorus oxychloride in the presence of dimethylformamide. The latter is subsequently converted into the desired product using aqueous propionic acid.

The disadvantages of this process are, on the one hand, the moderate yield of desired product and, on the other hand, the fact that this process proceeds via 3 stages.

To date, a number of processes for the preparation of 2,5-diamino-4,6-dihalopyrimidines such as 2,5-diamino-4,6-dichloropyrimidine have also been disclosed. For example, WO 91/01310 describes a process for the preparation of 2,5-diamino-4,6-dichloro-pyrimidine starting from 2,5-diamino-4,6-dihydroxy-pyrimidine in the presence of phosphorus oxychloride and a quaternary ammonium halide or a weakly basic tertiary amine or its salt. In this process, the phosphorus oxychloride serves as a solvent. This process has the disadvantage that is not reproducible on the industrial scale and the desired final product is only obtained in low yield.

The object of the present invention was to make available a simpler process for the preparation of N-(amino-4,6-dihalopyrimidine) formamides, in which the desired product is obtained in good yield.

Surprisingly, it has now been found that if a 2,5-diamino-4,6-dihalopyrimidine of the general formula

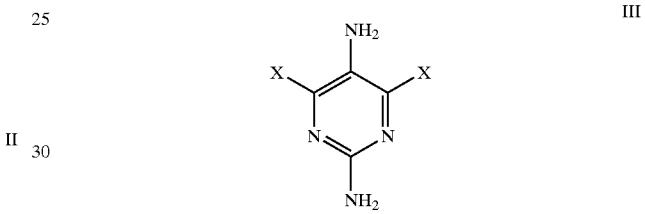

in which X is a halogen atom is reacted with formic acid, the final products of the general formula I or II are obtained directly, i.e. without intermediates, in excellent yield.

Cl or Br can be employed as the halogen atom, preferably Cl is employed. Accordingly, 2,5-diamino-4,6-dichloro- or 2,5diamino-4,6-dibromopyrimidine is preferably employed as the 2,5-diamino-4,6-dihalopyrimidine.

The formic acid employed below is a least 70–98% strength formic acid.

Expediantly, if the preparation of the product of the formula I is desired, a 70–80% strength formic acid is employed and the reaction is carried out at a temperature of 20° C. to 60° C., preferably of 25° C. to 55° C.

If the preparation of the product of the formula II is desired, expediently an 80–98% strength formic acid is employed and the reaction is carried out at a temperature of 0° C. to 30° C., preferably of 10 to 25° C.

Surprisingly, it has been found that the starting material 2,5-diamino-4,6-dihalopyrimidine of the general formula III is obtained in good yield if 2,5diamino-4,6-dihydroxypyrimidine its salt of the formula

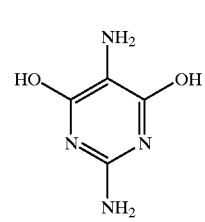

is reacted with a halogenated hydrocarbon as a solvent in the presence of a phosphorus oxyhalide and a quaternary ammonium halide or an amine.

2,5-Diamino-4,6-dihydroxypyrimidine is a commercially available compound. A suitable 2,5-diamino-4,6-dihydroxypyrimidine is also its salts such as its hydrohalide salts such as the hydrochloride salts and hydrobromide salts.

The phosphorus oxyhalide employed is expediently phosphorus oxychloride or phosphorus oxybromide.

The amine used can be a primary, secondary or tertiary amine or its salts such as its hydrochloride or hydrobromide salts. The quaternary ammonium halide employed is expediently ammonium chloride ammonium bromide. Customarily, the amine or the quaternary ammonium halide is employed in an excess based on the 2,5-diamino-4,6-dihydroxypyrimidine, preferably 1 to 10 mol of amine are employed based on 1 mol of 2,5-diamino-4,6-dihydroxypyrimidine.

The reaction is expediently carried out at a temperature of 20° C. up to the reflux temperature of the appropriate solvent, preferably of 100 to 120° C.

The halogenated hydrocarbons used can be halogenated aliphatic hydrocarbons. Examples of halogenated aliphatic hydrocarbons are halogenated alkanes. The halogenated alkane employed can be a halogenated propane such as 1,2,3-trichloropropane.

The reaction can be conducted in a halogenated aliphatic hydrocarbon as a solvent and at the prefererred temperature of 100 to 120° C.

EXAMPLES

Example 1
Preparation of 2,5-diamino-4,6-dichloropyrimidine 2,5-Diamino-4,6-dihydroxypyrimidine hydrochloride (0.14 mol, 25 g) was filled into a dry reactor. Dry 1,2,3-trichloropropane (51.96 ml) was then added and the whole was stirred. Subsequently, tetra-methylammonium chloride (0.29 mol, 31.25 g) and then POCl$_3$ (0.54–0.81 mol, 124.9–83.28 g, 50.6–75.9 ml) were added. The reaction was heated at reflux temperature (about 115° C.) for 24 h. The reaction was then cooled to below 50° C., ice water (24.44 mol, 440.44 g) was added and the whole was kept below 55° C. Subsequently, the reaction was adjusted to a pH of between 6.5 and 7.0 using 50% strength NaOH (3.12 mol, 124.92 g, 163.3 ml) and the temperature was kept below 55° C. The reaction was stirred at between 50 and 60° C. for 30 min. Tetrahydrofuran (3.7 mol, 267.0 g, 300 ml) was then added. In order to remove undesired material, the whole mixture was filtered through Celite and the filter cake was then washed with ethyl acetate (20.5 mol, 1806.58 g, 2002.86 ml) for subsequent extraction. The organic phase (tetrahydrofuran and ethyl acetate) was washed 3 times with water (5.57 mol, 100.32 g, 100.32 l), dried over NaHCO$_3$ and filtered. Ethyl acetate was removed by vacuum distillation. Hexane (0.77 mol, 66.14 g, 100.36 ml) was then added to the residual organic material, and the whole was cooled to below 10° C., filtered and then dried at 50° C. in vacuo. The title product (0.09 mol, 15.71 g) was obtained as a slightly brownish solid, corresponding to a yield of about 65% based on 2,5-diamino-4,6-dihydroxypyrimidine employed.

Example 2
Preparation of N-(2-amino-4,6-dichloropyrimidin-5-yl)-formamide 2,5-Diamino-4,6-dichloropyrimidine (0.01 mol; 2.0 g) and water (0.25 mol; 4.55 ml) were stirred at room temperature. 98% strength formic acid (0.4 mol; 18.27 g; 14.97 ml) was then added to the reaction. The reaction was subsequently heated to 50–55° C. and kept at this temperature for 3 h. Toluene (0.38 mol; 34.6 g; 40 ml) was then added for the azeotropic distillation under high vacuum at 50° C. (toluene was added twice to guarantee a good distillation, i.e. a total of 80 ml).

The product was subsequently filtered, washed with water and then dried at 60° C. in vacuo. 0.01 mol (2.0 g) of the abovementioned product was obtained, corresponding to a yield of about 90%.

Example 3
Preparation of N-(5-amino-4,6-dichloropyrimidin-2-yl)-formamide

A solution of 2,5-diamino-4,6-dichloro-pyrimidine (0.001 mol; 2.0 g) and 98% strength formic acid (0.5 mol, 22.96 g, 18.8 ml) was stirred overnight at room temperature. Toluene (0.94 mol, 86.76 g, 18.82 ml) was then added and the reaction was cooled to 0–5° C. The product was filtered off and washed with water (1.11 mol, 20.0 g, 20.0 ml). The product was subsequently dried at 50° C. in vacuo. N-(5-Amino-4,6-dichloropyrimidin-2-yl)formamide was detected in the $^1$H NMR as a single product. 0.01 mol (1.62 g) of the abovementioned product was obtained, corresponding to a yield of about 70%.

What is claimed is:

1. A process for the preparation of 2,5-diamino-4,6-dihalopyridine of the formula:

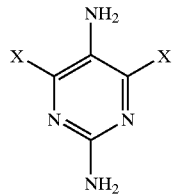

III in which X is a halogen atom, comprising reacting 2,5-diamino-4,6-dihydroxypyrimidine or its salt of the formula:

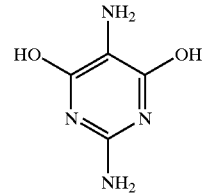

IV with a phosphorus oxyhalide and a quaternary ammonium halide in a halogenated aliphatic hydrocarbon as a solvent and at a temperature of 100 to 120° C.

2. The process according to claim 1 wherein the solvent is a halogenated alkane.

3. The process according to claim 1 wherein the salt of 2,5-diamino-4,6-dihydroxypyrimidine is a hydrohalide salt.

4. The process according to claim 1 wherein an excess of the quaternary ammonium halide is used.

5. The process according to claim 1 wherein in the phosphorus oxyhalide is phosphorus oxychloride or phosphorus oxybromide.

6. The process according to claim 3 wherein the hydrohalide salt is a hydrochloride salt or a hydrobromide salt.

7. The process according to claim 1 wherein the 2,5-diamino-4,6-dihalopyrimidine of formula III is 2,5-diamino-4,6-dichloropyrimidine or 2,5-diamino-4,6-dibromopyrimidine.

8. The process according to claim 1 wherein the solvent is halogenated propane.

9. The process according to claim 1 wherein the solvent is 1,2,3-trichloropropane.

10. The process according to claim 1, wherein the reaction is of 2,5-diamino-4,6-dihydroxypyrimidine hydrochloride in the presence of 1,2,3-trichloropropane, tetramethylammonium chloride and POCl$_3$ at reflux temperature of about 115° C., reaction mixture is cooled to below 55° C., pH of the reaction mixture is adjusted to between 6.5 and 7.0, and the 2,5-diamino-4,6-dichloropyrimidine is separated from the reaction mixture.

11. The process according to claim 1 wherein the halogenated aliphatic hydrocarbon is a trichloropropane.

* * * * *